United States Patent [19]

Shinohara et al.

[11] 4,200,736
[45] Apr. 29, 1980

[54] PREPARATION OF WATER-INSOLUBLE CARBOXYMETHYL CELLULOSE ABSORBENTS

[75] Inventors: Makoto Shinohara, Ringwood; Nathan D. Field, Wyckoff, both of N.J.

[73] Assignee: International Playtex, Inc., Stamford, Conn.

[21] Appl. No.: 906,723

[22] Filed: May 17, 1978

[51] Int. Cl.² ............................................. C08B 11/20
[52] U.S. Cl. ...................................... 536/87; 536/88; 536/98
[58] Field of Search .................. 536/98, 85, 87, 88

[56] References Cited
U.S. PATENT DOCUMENTS

| | | |
|---|---|---|
| 2,447,757 | 8/1948 | Lilienfeld ................................ 536/87 |
| 2,639,239 | 5/1953 | Elliott ................................ 106/197 C |
| 2,766,137 | 10/1956 | Ashton et al. .......................... 536/98 |
| 3,322,748 | 5/1967 | Tokimatsu et al. ..................... 536/98 |
| 3,379,721 | 4/1968 | Reid ....................................... 536/87 |
| 3,731,686 | 5/1973 | Chatterjee .............................. 536/87 |

*Primary Examiner*—Ronald W. Griffin
*Attorney, Agent, or Firm*—Stewart J. Fried; Jeffrey A. Schwab

[57] ABSTRACT

A process for the preparation of a substantially water-insoluble, particulate sodium salt of carboxymethyl cellulose, suitable for use as an absorbent in tampons and other catamenial devices or the like. The process involves heating solid, water-soluble sodium carboxymethyl cellulose, having a degree of substitution of at least 0.4, with carbon dioxide gas to substantially insolubilize the carboxymethyl cellulose and convert it to a form suitable for absorbent applications.

8 Claims, 1 Drawing Figure

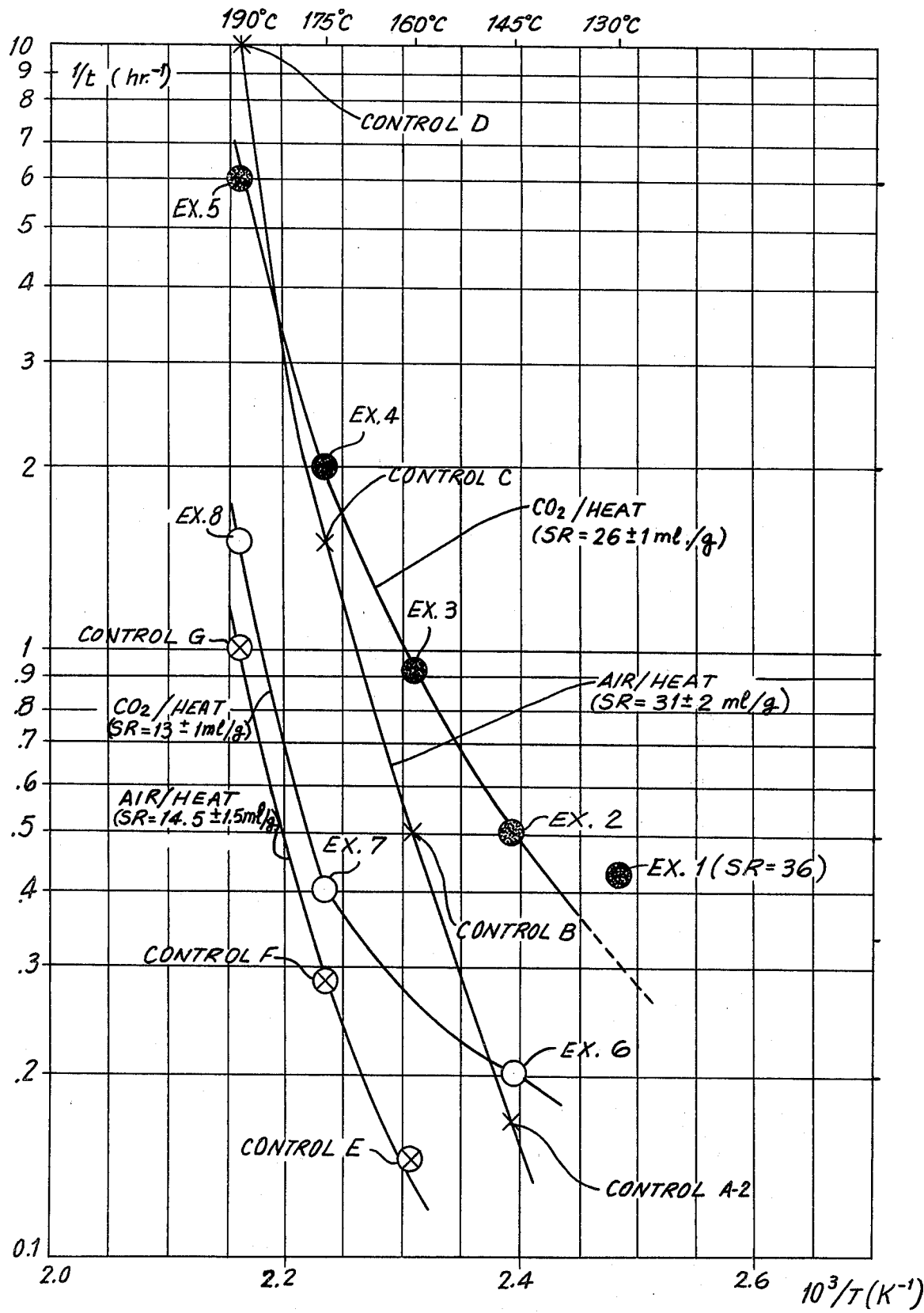

PREPARATION OF WATER-INSOLUBLE CARBOXYMETHYL CELLULOSE ABSORBENTS

BACKGROUND OF THE INVENTION

The present invention relates to an improved method for the preparation of water-insoluble carboxymethyl cellulose (CMC) absorbents.

The use of CMC as an absorbent material in catamenial devices or other absorbent dressings has been known in the literature for a number of years. See, for example, Masci et al U.S. Pat. Nos. 2,764,159 and 2,772,999 granted on Sept. 25 and Dec. 4, 1956, respectively; Ashton et al U.S. Pat. No. 2,766,137 granted Oct. 9, 1956; Graham U.S. Pat. No. 3,005,456 granted Oct. 24, 1961; Burgeni et al U.S. Pat. No. 3,067,745 granted Dec. 11, 1962; and Lewing U.S. Pat. No. 3,371,666 granted Mar. 5, 1968.

Graham disclosed that only CMC's having a DS value (the number of carboxymethyl groups per anhydroglucose unit in the cellulose chain) less than about 0.35 are useful as absorbents, and described those materials having higher DS values as too soluble for such purpose. It has, however, subsequently been disclosed that CMC's having higher DS values are also suitable for use in absorbent dressings, particularly if insolubilized, e.g., by cross-linking. In this connection reference may be made, for example, to the aforesaid Ashton et al and Masci et al patents; Elliot U.S. Pat. No. 2,639,239 granted May 19, 1953; Dean et al U.S. Pat. No. 3,589,364 granted June 29, 1971; Ells et al U.S. Pat. No. 3,618,607, granted Nov. 9, 1971; Schoggen U.S. Pat. No. 3,678,031, granted July 18, 1972; Chatterjee U.S. Pat. No. 3,731,686, granted May 8, 1973; and Kaczmarzyk et al U.S. Pat. No. 4,044,766, granted Aug. 30, 1977. One commonly used procedure which has been proposed for preparing water-insoluble CMC's involves insolubilizing the material merely by heat-catalyzed cross-linking. See, for example, the aforesaid Chatterjee patent, and Reid U.S. Pat. No. 3,379,720 granted Apr. 23, 1968.

Material thus insolubilized may be in the salt form, or the carboxylate moieties thereof may be partially acidified and the polymer thus placed in the so-called "acid form". Insolubilized CMC's in both the salt (see, for example, the aforesaid Chatterjee and Kaczmarzyk patents) and acid forms (see, for example, the aforesaid Ashton et al and Masci et al patents) have been described as suitable for use as absorbents for dressing materials.

Copending application Ser. No. 906,724 entitled, "Preparation of Water-Insoluble Carboxymethyl Cellulose Absorbents", in the names of Herman Marder, Nathan Field and Makoto Shinohara describes an improved process for the preparation of acid-form CMC's suitable for application as absorbents. The present invention, on the other hand, is directed to an improved technique for the production of CMC salt absorbents.

It is, accordingly, a principal object of the present invention to provide an improved process for the preparation of water-insoluble CMC materials in the salt form, the products of which may be readily utilized as absorbents for catamenial devices and other absorbent dressings.

Other objects and advantages of the process of the invention will be apparent from the following description of preferred embodiments thereof, considered in connection with the annexed graphical drawing illustrating the reaction temperatures and times necessary for insolubilizing CMC salts employing the process of the invention.

SUMMARY OF THE INVENTION

In accordance herewith, a process is provided for the preparation of substantially water-insoluble, particulate CMC suitable for application as an absorbent material. The process involves the direct heating of a solid, water-soluble particulate sodium CMC, having a DS value of at least about 0.4 in the presence of carbon dioxide gas, to thereby substantially insolubilize the carboxymethyl cellulose.

By proceeding in this manner, water-soluble sodium CMC's having DS values of as low as about 0.4, and generally from about 0.5 to 1.2, may be readily insolubilized. Suitable regulation of the DS values of the materials reacted facilitates the formation of insoluble CMC's which exhibit swell ratios of from as low as 5 to as much as 50, and which have percent extractables (soluble contents) of less than about 40 percent.

The insolubilized CMC's thus produced, when incorporated as absorbents in tampons, other catamenial devices, or other absorbent products, exhibit characteristics comparable to those of insolubilized CMC materials produced by other techniques. Moreover, the $CO_2$ gas treatment of the invention appears to catalyze the transformation of the soluble CMC salt and result in insolubilization thereof under milder reaction time/temperature cycles than heretofore required, and providing products which are subject to lesser discoloration and degradation than prior art CMC's. In addition, the process hereof does not necessitate the use of expensive process equipment (as may be necessary in processes utilizing strongly acid media for preparing acid-form CMC's), nor require extensive solvent recovery operations or entail environmental problems (such as posed by various slurry techniques for insolubilizing CMC materials). The combined $CO_2$ gas/heat treatment technique of the present invention thus appears to effect the desired insolubilization of the initially soluble CMC salt treated more efficiently, with less concomitant problems, and more rapidly (under the same reaction conditions) than required by prior art processes.

It is possible that insolubilization of the CMC occurs by a cross-linking reaction which may be characterized, at least in part, as follows:

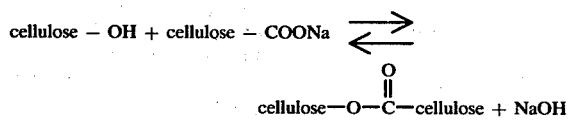

$$\text{cellulose} - \text{OH} + \text{cellulose} - \text{COONa} \rightleftarrows \text{cellulose} - \text{O} - \overset{\overset{\displaystyle O}{\|}}{\text{C}} - \text{cellulose} + \text{NaOH}$$

The $CO_2$ gas added in the practice of the present invention may react with the sodium hydroxide thus produced, forming sodium bicarbonate, and shifting the equilibrium of the cross-linking reaction toward completion.

It is also possible that the $CO_2$ contact step of the invention has a purely catalytic effect on the insolubilization reaction. Thus, in marked contrast to prior art procedures in which $CO_2$ has been added as a precipitant to CMC-containing dispersions (see Lilienfeld U.S. Pat. No. 2,447,757 granted Aug. 24, 1948), or in which it may be generated from a neutralizing or forming agent added at other stages in the processing of CMC materials (see Bauling et al U.S. Pat. No. 2,711,407 granted June 21, 1955, and Smith U.S. Pat. No. 3,122,479 granted Feb. 25, 1964), the heterogeneous solid-vapor contact effected during the combined $CO_2$/heat treatment of the present invention may have a catalytic effect where insolubilization occurs in the polymer.

The precise reaction mechanism which takes place in the practice of the process of the invention, whether any or all of the preceding, is not currently known. It should, therefore, be understood that the mechanisms postulated hereinabove are but possible explanations for the results achieved by the invention, and that the process hereof is not restricted to any of the reaction mechanisms posited. Rather, it is intended that the scope of the present invention solely be determined from the limitations of the claims appended hereto.

Heating of the carboxymethyl cellulose with simultaneous contact with carbon dioxide gas is carried out, in accordance with the invention, at temperatures in excess of about 100° C., preferably within the range of from about 120°–190° C., and for reaction times varying inversely with the temperature. In contrast, it has been found that the same catalytic effect is not achieved when, for example, the soluble CMC is contacted with other gases under elevated temperature conditions, or when the CMC is contacted with $CO_2$ under ambient conditions prior to effecting heat cross-linking. The soluble CMC may be contacted with carbon dioxide either by passing the gas over or through the particulate CMC material, or by maintaining a stagnant charge or blanket of the $CO_2$ gas over the solid material. In either event, the $CO_2$ may comprise from 20 to 100 percent by volume of the ambient atmosphere in the reaction zone, as may be desired.

PREFERRED EMBODIMENTS OF THE INVENTION

Any water-soluble, particulate carboxymethyl cellulose salt may be insolubilized in the practice of the present invention. Preferably, the process is carried out employing water-soluble sodium CMC's having DS values of at least 0.4, most desirably from about 0.5 to 1.2, and the reaction parameters are so regulated as to produce insolubilized CMC. Products thus formed have swell ratios (the degree of swelling with a saline solution as quantitatively defined below) ranging from about 5 to 50, preferably from about 5 to 40 (optimally about 10 to 35). Such products are, moreover, substantially water-insoluble, the percent extractables determined by extraction with a saline solution, as quantitatively defined hereinafter, being less than about 40% and, preferably less than about 35%.

The specific reaction parameters utilized, i.e., the time and temperature conditions, and the gas flow rates utilized in the carbon dioxide heat cross-linking operation (if continuous gas flows are used) are dependent upon a number of different variables, including the DS value of the soluble sodium CMC reacted and the desired characteristics of the insolubilized products in addition to the production rate required and, of course, the temperature-dependent degradation rate of the CMC. The particular conditions chosen depend, therefore, both upon the specific characteristics of the absorbent, water-insoluble CMC product desired, and the use of the most efficient reaction parameters for the desired operation.

As noted hereinabove, the $CO_2$ gas/heat insolubilization treatment may be carried out at temperatures varying from about 120° C. to as much as about 190° C. for inversely varying reaction periods. Preferably, the heat treatment is conducted at temperatures of from about 125° to 180° C.

A number of preferred embodiments of the present invention are illustrated in the following examples. Unless otherwise indicated therein, all temperatures are specified in degrees Celsius and all parts and percentages are given by weight.

EXAMPLES 1–5:

Comparison of Conditions Required with $CO_2$ Treatment of the Invention and in Air to Produce Insolubilized CMC's The following examples illustrate the enhanced insolubilization of dry, particulate sodium CMC (Hercules' 7HCF, having a DS of 0.7 and a water content of 7.1%) by heating in $CO_2$. Employing the $CO_2$ heat treatment of the invention, the reaction time required to effect insolubilization to a SR of 26±1 ml/g in $CO_2$ was materially shorter than the reaction time needed to effect insolubilization in air to a SR of 31±2 ml/g at a given temperature below 190° C., the catalytic effect of $CO_2$ treatment varying inversely with the temperature of insolubilization.

The insolubilization of the sodium CMC at 130° C. in $CO_2$ (Example 1) gave an insolubilized CMC with a SR of 36 ml/g in 2⅛ hours, while treatment at 145° C. in air (Control A-1) gave a sodium CMC with a SR of 40 ml/g in 5 hours. Hence, it may be seen that the $CO_2$ treatment effected more rapid and increased reaction at a lower reaction temperature.

With one exception, the insolubilization was effected by placing the soluble CMC (340 g) in a one liter three neck flask equipped with a mechanical stirrer, a gas inlet tube, a gas outlet tube, and a thermometer. The gas inlet tube was sufficiently long that its end was about 0.5–1 cm below the surface of the CMC particles, and the gas (either $CO_2$ or air) at ambient temperature was fed through the tube into the CMC at 1 to 4 l/minute monitored with a gas flow meter. While the CMC particles were mechanically agitated and the gas was pressured into the reaction zone, the CMC temperature was increased to the desired level (within 20 minutes to 145° C. or 40 minutes to 190° C.), and subsequently maintained (±5° C.) for the period of time specified in Table I below.

Heating was carried out by a heating mantle whose heat output was controlled by a termperature controller activated by the thermometer.

In the sole exception (Control B), the soluble CMC (130 g) was spread on two pans (43 cm×12 cm) at a depth of about 0.3 cm, was placed in an air circulating oven which had been preheated to 160° C., and was thereafter baked for 2 hours at that temperature.

The average SR's (swell ratio) and extractables of the products thereby formed were determined as follows:

Percent Extractables:

The percent extractables value for each sample was determined by placing 0.4–0.5 g. of the sample in a 100 ml. saline solution (0.85%) and mixing for 10 minutes, and decanting it into centrifuge tubes. After centrifuging for 10 minutes at 1500–1700 G's, a 25 ml sample was pipetted into a weighed beaker 25 ml of a blank—a 0.85% saline solution—was pipetted into a weighed beaker. After maintaining both the sample and the blank in a forced air oven overnight at 105° C. the percent extractables was determined by weighing the two materials and calculating the percent extractables as follows:

$$\text{Percent Extractables} = (400) \left[ \frac{\text{Total sample residue} - \text{Blank residue}}{\text{Bone dry sample weight}} \right]$$

Swell Ratios:

The product swell ratios (SR) were calculated by placing 1.00 gram ±0.01 gram of each of the respective samples in a 50 ml. graduated cylinder, filling the cylinder to the 50 ml. mark with a saline solution (0.85%), and shaking the cylinder several times. After a predetermined period (48 hours, unless otherwise indicated) the mark to which the sample had swelled was recorded and the swell ratio calculated as:

$$SR = \frac{\text{ml. (sample swelled)}}{\text{Bone dry sample weight}}$$

The conditions thus employed, and the properties so determined, were as follows:

TABLE I

COMPARATIVE DATA FOR HEAT TREATMENT WITH $CO_2$ AND IN AIR TO PRODUCE INSOLUBILIZED CMC'S

| Example | Reaction Conditions | | | SR (ml/g) | Ext. (%) |
| --- | --- | --- | --- | --- | --- |
| | Atmosphere | Temp. (°C.) | Time (hr.) | | |
| 1 | $CO_2$ | 130 | 2¼ | 36 | — |
| 2[a] | " | 145 | 2 | 25 | 17 |
| 3 | " | 160 | 1-1/12 | 26 | — |
| 4 | " | 175 | ½ | 27 | — |
| 5 | " | 190 | 1/16 | 27 | — |
| Control A-1[b] | Air | 145 | 5 | 40 | 30 |
| Control A-2 | " | 145 | 6 | 30 | — |
| Control B[c] | " | 160 | 2 | 29 | 21 |
| Control C | " | 175 | ⅞ | 31 | — |
| Control D | " | 190 | 1/10 | 33 | — |

[a]The flow rate of $CO_2$ was 1 l/min instead of 4 l/min., and its SR was determined at 21 hours.
[b]The flow rate of air was 1 l/minute instead of 4 l/minute.
[c]Total reaction time in an air circulating oven, and its SR was determined at 19.5 hours.

EXAMPLES 6–8:

Comparison of Conditions Required with $CO_2$ Treatment of the Invention and in Air to Produce Insolubilized CMC's Having SR's of About 13

The conditions required to convert soluble CMC (7HCF) to insolubilized CMC's having SR's of 12–16 ml/g are illustrated in these examples.

Substantially the same reaction technique described in connection with Examples 1–5, save for minor variations in two experiments (Example 6 and Control G). The specific conditions employed, together with the properties exhibited by the insolubilized products formed, are indicated in Table II below.

A longer reaction time at a given temperature was necessary for the formation of the CMC's with the lower SR [compare Examples 6–8, with Examples 2, 4 and 5 ($CO_2$); and Controls E-G with Controls B-D (air)]. Insolubilization proceeded with shorter reaction times in $CO_2$ than in air, the effect of the carbon dioxide treatment being more pronounced at lower temperatures. The degree of discoloration was only moderate (slightly amber) for the insolubilized CMC of Example 6, and was extensive (amber to dark amber) for the insolubilized CMC's of Examples 7 and 8 and Controls E-G.

TABLE II

COMPARATIVE DATA FOR HEAT TREATMENT WITH $CO_2$ AND IN AIR TO PRODUCE CMC'S HAVING SR'S OF ABOUT 13

| Example or Control | Reaction Conditions | | | SR (ml/g) | Ext. (%) |
| --- | --- | --- | --- | --- | --- |
| | Atmosphere | Temp. (°C.) | Time (hrs) | | |
| Example 6[a] | $CO_2$ | 145 | 5 | 14 | 10 |
| Example 7 | $CO_2$ | 175 | 2½ | 12 | 11 |
| Example 8 | $CO_2$ | 190 | ⅞ | 12 | 14 |
| Control E | Air | 160 | 7 | 16 | 13 |
| Control F | Air | 175 | 3½ | 13 | 14 |
| Control G | Air | 190 | 1[b] | 13 | — |

[a]The $CO_2$ flow rate was 1.0–1.4 l/min. rather than 4 l/min., and the SR was determined at 21 hours.
[b]Total residence time in an air circulating oven.

The time/temperature cycles required to form the insolubilized products of Examples 1–8 and Controls A-1 through G are shown in the attached drawing, wherein the reciprocals of the reaction times $[1/t(hr.^{-1})]$ and temperatures $[10^3/T\ (°K.^{-1})]$ are plotted against one another. From the displacement of the curves representing the $CO_2$/heat treatment data relative to the air/heat treat data it is apparent that when the $CO_2$ gas treatment of the invention is utilized a given insolubilized CMC may be formed employing a shorter reaction time and/or lower reaction temperature than when the same product is formed by heat treatment in air. For example, when it is desired to form a CMC product having a swell ratio of about 25 ml/g at a reaction temperature of about 145° C., under the conditions of the examples about a 2 hour reaction time is required employing the $CO_2$ treatment of the invention (see the point marked Example 2 in the drawing), whereas more than about 6 hours are required when insolubilization is carried out in air (see the point marked Control A-2 in the drawing). Conversely, when it is wished to produce such a product in 2 hours reaction time, the reaction can be carried out at about 145° C. employing the $CO_2$ treatment hereof (see the point marked Example 2 in the drawing), whereas the reaction must be carried out at 160° C. or slightly higher if effected in air (see the point marked Control B in the drawing).

EXAMPLES 9–10:

Insolubilization Under $CO_2$ Blanket

Soluble CMC (7HCF) was insolubilized at 145° C. (Example 9) and at 160° C. (Example 10) under a relatively stagnant $CO_2$ atmosphere (about 1 cm with mineral oil), as distinguished from the continuous $CO_2$ throughputs utilized in the above experiments. The use of a slightly pressurized carbon dioxide atmosphere substantially reduced the consumption of $CO_2$ (to about 1/5 or less than expended with a continuous sweep of the gas), without substantially retarding the insolubilization reaction.

The soluble CMC (340 g) was initially heated to the desired temperature over a 20–30 minute period in a highly purified, sweeping nitrogen atmosphere. While the CMC was maintained at the elevated temperature, $CO_2$ was passed therethrough at a rate of 4 l/minute for ten minutes to purge it of nitrogen. Thereafter, the gas outlet tube was closed, the $CO_2$ pressure was maintained slightly above atmospheric pressure (about 1 cm with mineral oil), and the CMC was heated at the designated temperature for the remainder of the pre-determined time period.

The insoluble CMC's thus formed exhibited SR's and extractables which were essentially the same as those obtained employing continuous $CO_2$ sweeps, as indicated in the following table:

TABLE III

CMC INSOLUBILIZATION UNDER A $CO_{BLANKET}$

| | Reaction Conditions | | | |
|---|---|---|---|---|
| Example | Atmosphere | Temp (°C.) | Time (hrs) | SR (ml/g) | Ext. (%) |
| 2 | $CO_2$ sweep[a] | 145 | 1½ | 34 | 20 |
| 3 | $CO_2$ sweep | 160 | 5/6 | 34 | 21 |
| 9 | $CO_2$ blanket | 145 | 1½ | 37[b] | 26 |
| 10 | $CO_2$ blanket | 160 | 11/12 | 28 | — |

[a] $CO_2$ flow rate = 4 l/min.
[b] SR determined after 24 hours.

EXAMPLES 11–14:

Insolubilization with Partial $CO_2$ Atmospheres

Solid, particulate sodium CMC (7HCF) was insolubilized at 160° C. for 1½ hours in the following atmospheres swept therethrough at a rate of 4 l/minute: Example 11—100% $CO_2$; Example 12—60% $CO_2$/40% air; Example 13—40% $CO_2$/60% air; Example 14—20% $CO_2$/80% air; and Control H—100% air. The insolubilization was carried out employing the specific heat-treat procedure described in connection with Examples 1–5 above except that the $CO_2$ was introduced about 2 inches above the surface of the CMC.

The SR values and % extractables exhibited by the products thus obtained were as follows:

TABLE IV

INSOLUBILIZATION WITH ATMOSPHERES INCORPORATING VARYING PROPORTIONS OF $CO_2$

| Example or Control | Composition of Sweeping Atmosphere $CO_2$/Air (V/V) | Sr (ml/g) | Ext (%) |
|---|---|---|---|
| Example 11 | 100/0 | 30 | 22 |
| Example 12 | 60/40 | 33 | 19 |
| Example 13 | 40/60 | 29 | 21 |

TABLE IV-continued

INSOLUBILIZATION WITH ATMOSPHERES INCORPORATING VARYING PROPORTIONS OF $CO_2$

| Example or Control | Composition of Sweeping Atmosphere $CO_2$/Air (V/V) | Sr (ml/g) | Ext (%) |
|---|---|---|---|
| Example 14 | 20/80 | ess. sol. | (38) |
| Control H | 0/100 | ess. sol. | (41) |

Since the various changes may be made in the preferred embodiments of the process described hereinabove, it is intended that the preceding description should be construed as illustrative only, and that the scope of this invention should rather be determined from the claims appended hereto.

What is claimed is:

1. A process for the preparation of substantially water-insoluble, particulate carboxymethyl cellulose, which comprises heating a solid, water-soluble, particulate sodium carboxymethyl cellulose having a degree of substitution of at least 0.4 at temperatures in excess of 100° C. and in the presence of carbon dioxide gas, to thereby substantially insolubilize the carboxymethyl cellulose, the thus insolubilized carboxymethyl cellulose exhibiting a swell ratio of from 5 to 50.

2. The process of claim 1, wherein the insolubilized sodium carboxymethyl cellulose has an extractables content of less than 40%.

3. The process of claim 1, wherein the solid, water-soluble sodium carboxymethyl cellulose has a degree of substitution of from 0.5 to 1.2.

4. The process of claim 1, wherein the sodium carboxymethyl cellulose is heated at temperatures of from 120° to 190° C.

5. The process of claim 1, wherein the ambient atmosphere comprises at least 20% by volume carbon dioxide.

6. The process of claim 1, wherein the carbon dioxide gas is passed over or through the particulate sodium carboxymethyl cellulose.

7. The process of claim 1, wherein the particulate sodium carboxymethyl cellulose is contacted by a stagnant charge of the carbon dioxide gas.

8. The process of claim 1, wherein the soluble sodium carboxymethyl cellulose reacted has a degree of substitution of from 0.5 to 1.2, wherein the carboxymethyl cellulose is heated at temperatures of from 125° to 180° C., and wherein the insoluble sodium carboxymethyl cellulose produced exhibits a swell ratio of from 5 to 40 and an extractables content of less than 35%.

* * * * *